(12) United States Patent
Pawelzik et al.

(10) Patent No.: US 7,277,831 B1
(45) Date of Patent: Oct. 2, 2007

(54) METHOD FOR DETECTING TIME DEPENDENT MODES OF DYNAMIC SYSTEMS

(75) Inventors: Klaus Pawelzik, Bremen (DE); Klaus-Robert Müller, Berlin (DE); Jens Kohlmorgen, Berlin (DE)

(73) Assignee: Fraunhofer-Gesellschaft zur Forderung der angewandten Forschung e. V. (DE)

( * ) Notice: Subject to any disclaimer, the term of this patent is extended or adjusted under 35 U.S.C. 154(b) by 0 days.

(21) Appl. No.: 09/508,042

(22) PCT Filed: Sep. 11, 1998

(86) PCT No.: PCT/EP98/05793

§ 371 (c)(1),
(2), (4) Date: Apr. 28, 2000

(87) PCT Pub. No.: WO99/14686

PCT Pub. Date: Mar. 25, 1999

(30) Foreign Application Priority Data

Sep. 15, 1997 (DE) ................. 197 40 565

(51) Int. Cl.
*G06F 7/60* (2006.01)
*G06F 17/50* (2006.01)
*G06G 7/48* (2006.01)
*G06F 15/18* (2006.01)
*G06F 15/00* (2006.01)
*G06E 1/00* (2006.01)

(52) U.S. Cl. ............... 703/2; 706/6; 706/16; 706/22; 706/44; 703/6; 703/11; 703/13

(58) Field of Classification Search ............. 703/2, 703/13, 6, 11; 706/6, 16, 22, 44, 41, 14
See application file for complete search history.

(56) References Cited

U.S. PATENT DOCUMENTS 5,307,444 A    4/1994  Tsuboka (Continued)

FOREIGN PATENT DOCUMENTS

DE    195 30 646 C1    10/1996

(Continued)

OTHER PUBLICATIONS

Pawelzik et al., Quantifying the Neighborhood Preservation of Self-Organizing Feature Maps, IEEE 1992.*

(Continued)

*Primary Examiner*—Anthony Knight
*Assistant Examiner*—Tom Stevens
(74) *Attorney, Agent, or Firm*—DLA Piper US LLP (57) ABSTRACT

In a method for detecting the modes of a dynamic system with a large number of modes that each have a set $\alpha$ (t) of characteristic system parameters, a time series of at least one system variable x(t) is subjected to modeling, for example switch segmentation, so that in each time segment of a predetermined minimum length a predetermined prediction model, for example a neural network, for a system mode is detected for each system variable x(t), whereby modeling of the time series is followed by drift segmentation in which, in each time segment in which there is transition of the system from a first system mode to a second system mode, a series of mixed prediction models is detected produced by linear, paired superimposition of the prediction models of the two system modes.

26 Claims, 5 Drawing Sheets

U.S. PATENT DOCUMENTS

| | | | | |
|---|---|---|---|---|
| 5,412,163 | A | | 5/1995 | Tsuji |
| 5,479,571 | A | * | 12/1995 | Parlos et al. .................. 706/25 |
| 5,515,477 | A | * | 5/1996 | Sutherland ................... 706/41 |
| 5,659,667 | A | | 8/1997 | Buescher et al. |
| 5,748,847 | A | * | 5/1998 | Lo .............................. 706/14 |
| 5,796,922 | A | * | 8/1998 | Smith ......................... 706/23 |
| 5,995,868 | A | * | 11/1999 | Dorfmeister et al. ....... 600/544 |
| 6,014,468 | A | * | 1/2000 | McCarthy et al. .......... 382/254 |

FOREIGN PATENT DOCUMENTS

| | | |
|---|---|---|
| DE | 195 30 647 C1 | 1/1997 |
| DE | 195 31 967 A1 | 3/1997 |
| DE | 195 37 010 A1 | 4/1997 |
| EP | 0 510 632 A2 | 10/1992 |
| WO | WO 90/09644 | 8/1990 |
| WO | WO90/09644 | 8/1990 |
| WO | WO94/20887 | 9/1994 |
| WO | WO 94/20887 | 9/1994 |
| WO | WO 95/18420 | 7/1995 |
| WO | WO95/18420 | 7/1995 |

OTHER PUBLICATIONS

Pawelzik et al., Segmentation and Identification of Drifting Dynamic Systems, IEEE 1997.*

Kohlmorgen et al., "Segmentation and Identification of Drifting Dynamical System" 1997 IEEE p. 326-335.*

John Hertz et al., Introduction to the Theory of Neural Computation, Addition-Wesley Publishing Company, 1991, Chapter 9 "Unsupervised Competitive Learning".

G. Pfurtscheller et al., Sleep Classification in Infants Based on Artificial Neural Networks, Biomedizinische Technik, Band 37, Heft Jun. 1992, pp. 122-130.

Andreas Draeger et al., Prädiktive Regelung Verfahrenstechnischer Anlagen Mit Neuronalen Netzen, Automatisierungstechnische Praxis 37, 1995, 4, pp. 55-61 w/English language summary.

Dietmar Wetzlar. Neuronale Netze in Der Meβ Technik. Technisches Messen 62, 1995, 3 w/English language summary.

Achim Bothe, Neuronale Klassifikatoren in der Akustischen Mustererkennung, Technisches Messen 62, 1995, 3, pp. 88-94 w/English language summary.

Stephan Ester, Herzschallanalyse MTT Unterstützung Adaptiver Filter Und Neuronaler Netze, Technisches Messen 62, 1995, 3, pp. 107-112 w/English language summary.

Dietmar Gerhardt et al., Atemmuster- und Schlafstadienerkennung Mit Neuronalen Netzen Bei Säuglingen, Technisches Messen 62, 1995, 3, pp. 113-116 w/English language summary.

Christel Wisotzki et al., Lernfähige Klassifikation Von Zeitreihen, Automatisierungstechnik 43, 1995, 2, pp. 70-76 w/English language summary.

Stefan Gehlen et al., Einsatz Neuronaler Netze Zur Kontrolle Komplexer Industrieller Prozesse, Automatisierungstechnik 43, 1995, 2, pp. 85-91 w/English language summary.

Harald Peters, Anwendung Künstlicher Neuronaler Netze In Überwachungssystemen, Automatisierungstechnischebe Praxis 38, 1996, 11, pp. 37-38, 40-42, 44-46, 48 w/English language summary.

Thomas Martinetz et al., Neuronale Netze Zur Steuerung Von Walzstraben, Automatisierungstechnische Praxis 38, 1996, 10, pp. 28, 30-32, 34-36, 41-42 w/English language summary.

Klaus Pawelzik et al., Annealed Competition of Experts For a Segmentation and Classification of Switching Dynamics, Neural Computation 8, pp. 340-356, 1996.

D. Popivanov et al., Detection of Successive Changes in Dynamics of EEG Time Series: Linear and Nonlinear Approach, 18th Annual International Conference of the IEEE Engineering in Medicine and Biology Society, 1996, pp. 1590-1591.

J. Pardey et al., A Review of Parametric Modelling Techniques for EEG Analysis, Med. Eng. Phys., vol. 18, No. 1, pp. 2-11, 1996.

J. Kohlmorgen, et al., Analysis of Wake/Sleep EEG with Competing Experts, pp. 1077-1082.

N. H. Packard et al., Geometry From a Time Series, Physical Review Letters, vol. 45, No. 9, Sep. 1980, pp. 712-716.

Lawrence R. Rabiner, Fellow, IEEE, A Tutorial on Hidden Markov Models and Selected Applications in Speech Recognition, Readings in Speech Recognition, Eds. Alex Waibel et al., San Mateo, Morgan Kaufmann, 1990, pp. 267-296.

Muller, et al., "Analysing Physiological Data from Wake-Sleep Transition with Competing Predictors", 1995 p. 1-6.

Muller, et al., "Analysis of Switching Dynamics with Competing Neural Networks" Oct. 10, 1995 p. 1-11.

Kohlmorgen, et al., "Competing Predictors Segments and Identity Switching Dynamics", 1994 ICANN, p. 1-5.

John Hertz et al., Introduction to the Theory of Neural Computation, Addition-Wesley Publishing Company, 1991, Chapter 9 "Unsupervised Competitive Learning".

G. Pfurtscheller et al., Sleep Classification in Infants Based on Artificial Neural Networks, Biomedizinische Technik, Band 37, Heft Jun. 1992, pp. 122-130.

Andreas Draeger et al., Prädiktive Regelung Verfahrenstechnischer Anlagen Mit Neuronalen Netzen, Automatisierungstechnische Praxis 37, 1995, 4, pp. 55-61 w/English language summary.

Dietmar Wetzlar. Neuronale Netze in Der Meβ Technik. Technisches Messen 62, 1995, 3 w/English language summary, p. 1-2.

Achim Bothe, Neuronale Klassifikatoren in der Akustischen Mustererkennung, Technisches Messen 62, 1995, 3, pp. 88-94 w/English language summary.

Stephan Ester, Herzschallanalyse MTT Unterstützung Adaptiver Filter Und Neuronaler Netze, Technisches Messen 62, 1995, 3, pp. 107-112 w/English language summary.

D. Popivanov et al., Detection of Successive Changes in Dynamics of EEG Time Series: Linear and Nonlinear Approach, 18th Annual International Conference of the IEEE Engineering in Medicine and Biology Society, 1996, pp. 1590-1591.

J. Pardey et al., A Review of Parametric Modelling Techniques for EEG Analysis, Med. Eng. Phys., vol. 18, No. 1, pp. 2-11, 1996.

J. Kohlmorgen, et al., Analysis of Wake/Sleep EEG with Competing Experts, pp. 1077-1082, Aug. 10, 1997.

N. H. Packard et al., Geometry from a Time Series, Physical Review Letters, vol. 45, No. 9, Sep. 1980, pp. 712-716.

Lawrence R. Rabiner, Fellow, IEEE, A Tutorial on Hidden Markov Models and Selected Applications in Speech Recognition, Readings In Speech Recognition, Eds. Alex Waibel et al., San Mateo, Morgan Kaufmann, 1990, pp. 267-296.

John Hertz et al., Introduction to the Theory of Neural Computation, Addition-Wesley Publishing Company, 1991, Chapter 9 "Unsupervised Competitive Learning", p. 1-10.

G. Pfurtscheller et al., Sleep Classification in Infants Based on Artificial Neural Networks, Biomedizinische Technik, Band 37, Heft Jun. 1992, pp. 112-130.

Andreas Draeger et al., Prädiktive Regelung Verfahrenstechnischer Anlagen Nit Neuronalen Netzen, Automatisierungstechnische Praxis 37, 1995, 4, pp. 55-61 w/English language summary.

Dietmar Wetzlar. Neuronale Netze in Der Meβ Technik. Technisches Messen 62, 1995, 3 w/english language summary, p. 1-2.

Achim Bothe, Neuronale Klassifikatoren in der Akustischen Mustererkennung, Technisches Messen 62, 1995, 3, pp. 88-94 w/English language summary.

Stephan Ester, Herzschallanalyse MTT Unterstützung Adaptiver Filter Und Neuronaler Netze, Technisches Messen 62, 1995, 3, pp. 107-112 w/English language summary.

* cited by examiner

METHOD FOR DETECTING TIME DEPENDENT MODES OF DYNAMIC SYSTEMS

TECHNICAL FIELD

This disclosure concerns a method for detecting dynamic systems that can be characterized by system parameters being non-stationary in time, in particular a method for segmenting time series of measured quantities (variables) of dynamic systems and for identifying the system parameters (modes) that characterize the segments.

BACKGROUND

As a dynamic system is considered in this case, in particular, any phenomenon whose time characteristic can be represented in a discrete form of the type $$x(t+1) = f_{\alpha(t)}(\alpha(t)) \qquad (0.1)$$

Also looked at, however, are systems with several (eg two) simultaneously detected time series x, y according to $$y(t+\tau) = f_{\alpha(t)}(x(t)) \qquad (0.2)$$

wherein $\alpha(t)$ is a set of characteristic system parameters, x is a state that generally forms a vector in a multidimensional state space, and y is a state displaced in time. The state space is created by variables that, for example, can be physical, chemical, biological, medical, geological, geometric, numerical and/or process engineering quantities.

The number of system variables that describe the system together with the dynamic response f corresponds to the dimension of the state space. Systems are looked at here whose parameters $\alpha$ may also be variable in time. A given system with parameters $\alpha$ that are invariable in time is also referred to in what follows as a mode.

Observable or measurable system variables (measured quantities) form detectable time series or data streams that are characteristic of the particular sequence of system modes. If the system parameters are invariable for certain time segments within the time series, the time series can be split corresponding to the system modes (segmentation) and each segment can be allocated to a system mode (identification).

Many phenomena in nature as well as in technical applications could be predicted and/or controlled if their basic dynamic processes could be modeled mathematically. The analysis and characterization of practical dynamic systems are often hindered by the fact that the system modes alter while being observed. Examples of this are gradual changes that manifest themselves as drifts or trends of the system parameters, or spontaneous or abrupt changes in the dynamic response of complex systems, for instance when configurations change suddenly, spontaneously or driven from the exterior.

An example of a system considered is the generation of speech signals in the mouth/pharynx region, whereby the system constantly changes its configuration and thus its mode. There is considerable interest in detecting and identifying the modes that are the basis of an observed variable as a function of time (example: fluctuations in air pressure) in order to make better predictions of the system observed or to control it better.

Basically, dynamic systems can be analyzed by measured signals, and a number of methods are known for obtaining models from time series that are suitable for predicting and controlling the response of the system. It is known, for instance, that the state of a dynamic system can be modeled by detecting the time dependence of observed measured quantities. In a first approach this modeling is by reconstruction of the state space by means of so-called time delay coordinates, as described, for example, by N. H. Packard et al. in "Physical Review Letters", vol. 45, 1980, p 712 ff. Only a single (global) model f for the dynamic response can be found on the basis of such a reconstruction. The global reconstruction of the system is also a disadvantage in that, in applications for multidimensional systems, a large number of input variables must be known in advance as boundary conditions and/or, because of the high dimensionality, the system is virtually impossible to estimate (detect, map) and/or the computing effort is so excessive and quite impractical.

Furthermore, this method is generally inapplicable in the case of parameters that vary with time. The analysis and modeling of dynamic signals are frequently hindered by the fact that the basic systems change with time in essential parameters. Examples are signals in medicine where an organ like the heart or the brain has many dynamic modes that alternate, or speech signals where the generating system, the mouth/pharynx region, apparently adopts different configurations in the course of time.

Another approach is known from the publication by K. Pawelzik, J. Kohlmorgen and K.-R. Mueller in "Neural Computation", vol. 8, 1996, p 340 ff, where data streams are segmented according to initially unknown system modes changing with time by simulation with several competing models. The models are preferably formed by neural networks, each characteristic of a dynamic response and competing to write the individual points of the data stream by predetermined training rules.

With this method it is possible to break down a time series into segments of quasi-static dynamic response and, simultaneously, to identify models for these system modes from the time series.

Segmentation according to K. Pawelzik et al., details of which are given below, allows allocation of segments to certain system dynamic responses or modes and leads to detection of the data stream as an operation with discrete "switching" between the modes. This description of the parameter dynamic response of complex systems is an advance in terms of accuracy and segmenting different system states compared to the above mentioned global modeling. Nevertheless, the transition between different system states cannot be described satisfactorily. In the analysis of real systems in particular, eg medical applications, it has been found that segmentation is limited to certain cases with mode differences that are as clear as possible and with low noise, and in general is unreliable when the generating system changes with time.

Such changes with time of the generating system make the observable signals transient and mean that the systems, as a rule, can no longer be described by uniform models. If such changes of the system are sudden, one speaks of jump processes.

OBJECT OF THE INVENTION

It would be helpful to provide improved methods for detecting the modes of dynamic systems with transient system parameters, by which the restrictions of conventional methods can be overcome, and which in particular allow, with practicable effort and high reliability, automatic segmentation and identification of time series with an enhanced number of details.

SUMMARY OF THE INVENTION

Our disclosure is based on the idea of comprehending transitions between different modes of a dynamic system as intermediate modes of the system that represent paired linear interpolations of the output and end modes of the transition. The observed dynamic systems tend to move gradually from one mode into another instead of switching abruptly between modes. We identify such transitions between different modes in signals and the modes.

Consequently, in a method for detecting the modes of dynamic systems, eg, after switched segmentation of a time series of at least one of the system variables x(t) of the system, drift segmentation is undertaken where, in each time segment in which the system transits from a first system mode $s_i$ to a second system mode $s_j$, a succession of mixed prediction models $g_i$ is detected given by a linear, paired superimposition of the prediction models $f_{i,j}$ of the two system modes $s_{i,j}$.

We also provide a device for detecting a dynamic system with a large number of modes $s_i$, each with characteristic system parameters $\alpha(t)$. The device includes an arrangement for recording a time series of at least one of the system variables x(t) of the system, an arrangement of switch segmentation for detecting a predetermined prediction model $f_i$ for a system mode $s_i$ in each time segment of a predetermined minimum length for the system variables x(t), and an arrangement of drift segmentation with which a series of mixed prediction models $g_i$ is detected in each time segment in which the system transits from a first system mode $s_i$ to a second system mode $s_j$. The device can also include an arrangement for setting interpolation and segmentation parameters, comparator circuits for processing the prediction errors of prediction models, arrangements of display and signaling, and an arrangement of storage. The device can be a monitor for physiological data or physical or chemical process parameters.

We further provide an instrument that has great potential for use in many medical, scientific and technical sectors. The segmentation of signals accompanied by identification of the fundamental dynamic response shows the way to new possibilities of prediction and control also in essentially non-stationary systems.

Applications have shown that continuous transitions between system modes can be securely identified and that the fundamental dynamic responses can be described by the models with a precision that, in many cases, allows prediction of the system response. In many cases of non-stationary processes, we enable models to be identified that are suitable for control of the processes, these not being possible without considering the transience.

BRIEF DESCRIPTION OF THE DRAWINGS

Selected embodiments and further advantages are described in what follows with reference to the attached drawings, which show.

DETAILED DESCRIPTION OF THE INVENTION

Figure 1A:
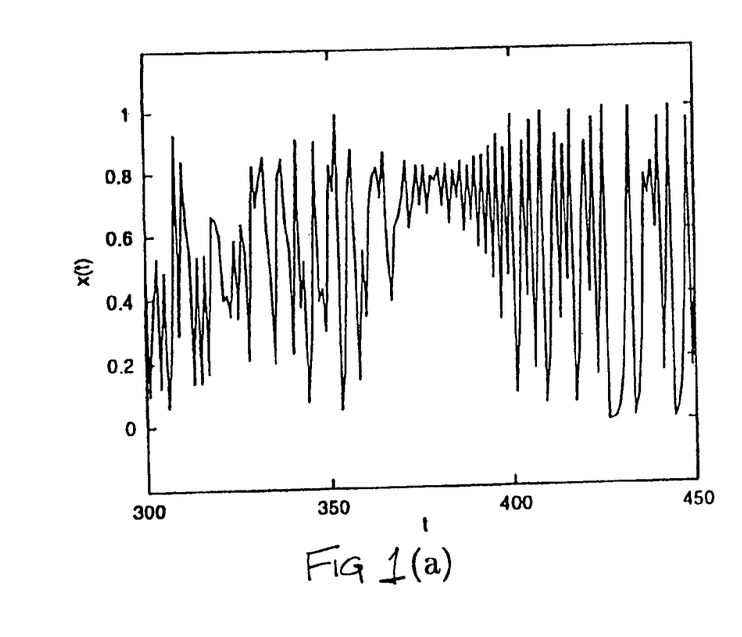
FIGS. 1a and b are graphs including curves illustrating a first segmentation step of the method, FIGS. 2a and b are graphs including curves illustrating a further segmentation step of the method.
Figure 1B:
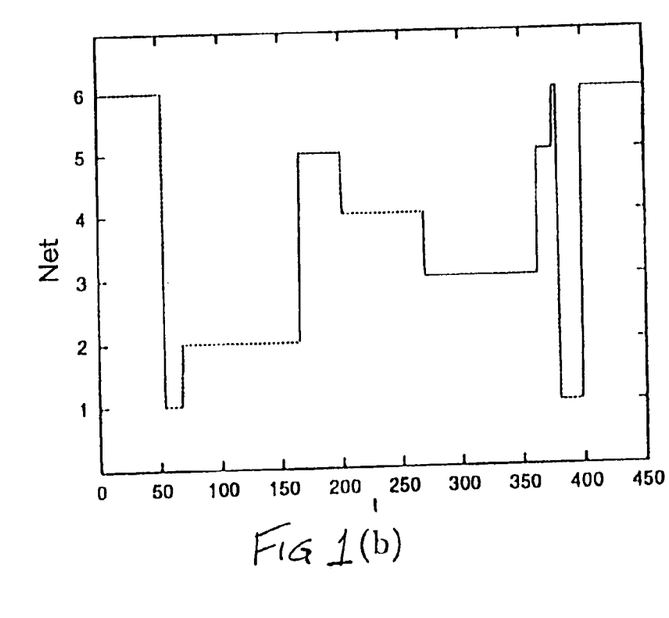
Figure 2:
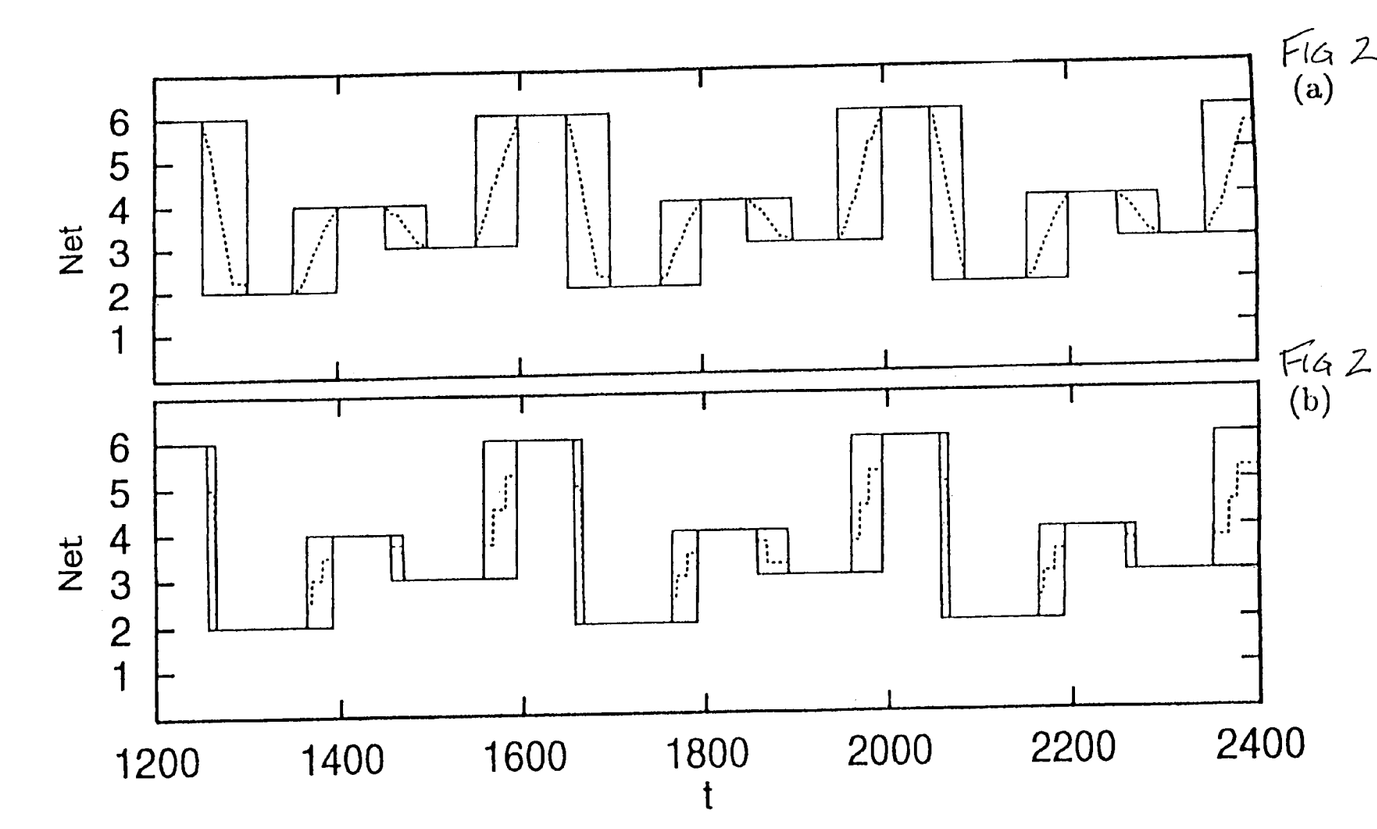

We first turn to FIGS. 1 and 2 and then examples of practical application. It will be clear to the skilled person that the subject matter of this disclosure is not restricted to the application examples but may also be used in other areas as exemplified further below.

(1) Detection of Drift Transitions in Non-Stationary Time Series

Non-stationary time series are detected by a procedure in two steps: first suitable modeling and then so-called drift segmentation. The purpose of the modeling is to detect a predetermined prediction model for a system mode in each time segment of a predetermined minimum length for each system parameter. Here, a conventional switch segmentation is preferred as known, for example, from the publication by K. Pawelzik et al. in "Neural Computation", vol. 8, 1996, p 340 ff. Modeling is also possible by another, in relation to the derived system information for switch segmentation, equivalent procedure that is matched to a concrete application, for example for known pure modes or boundary conditions.

The steps involved in switched and drift segmentation will now be explained in more detail. Where switched segmentation is concerned, the contents of the publication by K. Pawelzik et al. are completely incorporated into the present specification by reference.

(i) Step 1 (Switch Segmentation)

Switch segmentation serves for determining characteristic predictors that are suitable for describing the system modes. Switch segmentation can be performed either on a training time series or on the time series to be investigated. In both cases the prediction models or predictors that are determined can be used for further, unknown time series.

A dynamic system is considered with a finite number N of different modes. Characteristic of the j order mode is a value (vector or set) $\alpha_j$ (t) of an observable system parameter that is to be modeled with a function $f_{i(t)}$ (i=1, ..., N) from a set of N functions f. The time series $\{x_t\}=x_j(t)$ of the system variables is considered and, as a function of time, the function $f_{i(t)}$ is sought for which $\{y_t\}=y_j(t)=f_{i(t)}(x_j(t))$ represents a new time series of points $y_j(t)$ to be predicted that, in relation to the system modes, has the same characteristics qualitatively as $\{x_t\}$. Through the change of the model function f as a function of time, the switch segmentation is found that subdivides the time series $\{x_t\}$ according to the changing system modes.

The functions f are derived as predictors (or prediction models, expert functions) from a set of networks with variable parameters by a suitable training program in which both the parameters of the networks and the segmentation are determined simultaneously. The term "network" is used here for all possible, suitable model functions, in other words preferably for neural networks but also for polynomials or linear function approximations for example. The optimum choice of a neural network is made according to the specific application. Preferably, networks with fast learning capability are used, eg RBF (radial basis function) networks of the type Moody-Darken.

Training is performed on the condition that the system modes do not change with each time increment but exhibit a lower switching rate so that a system mode is maintained for several time increments. The assumed limit of the switching rate or number of time increments for which a system mode is maintained is initially a free input parameter and can be selected according to the application in a suitable way, for example as a function of given empirical values or by a parameter matching strategy. In the parameter matching strategy it may be intended that an initial value is specified for the switching rate and used to determine a prediction error as discussed below. If the chosen switching rate is too high or too low, the overspecialization or underspecialization will lead to a prediction error that is too high. In continuation of the matching, the switching rate can then be optimized until the mean prediction error is below predetermined limits.

Training involves maximizing the probability W that the set of networks would produce the time series $\{x_t\}$. This is training with competitive learning, as described in the publication "Introduction to the theory of neural computation" by J. Hertz et al. (Addison-Wesley Publishing Company, 1991), especially chapter 9 "Unsupervised competitive learning". The application-dependent implementation of such training can be derived from this publication. The training rule of competitive learning on the basis of the error occurring in learning can be represented according to $$\frac{\partial \log W}{\partial f_i} \propto \left[ \frac{e^{-\beta(y-f_i)^2}}{\sum_j e^{-\beta(y-f_j)^2}} \right] (y - f_i) \qquad (1)$$

This training rule ensures that the learning speed (improvement of parameters) is highest for the functions f with the smallest distance from the target value y.

FIGS. 1a and b show the result of switch segmentation in an example of analysis of a chaotic time series $\{x_t\}$ with $x_{t+1}=f(x_t)$ between the four modes:

$f_1(x)=4x(1-x)$ for $x\in[0, 1]$ $f_2(x)=f_1(f_1(x))$ $f_3(x)=2x$ for $x\in[0, 0.5]$ or $f_3(x)=2(1-x)$ for $x\in[0.5, 1]$ $f_4(x)=f_3(f_3(x))$ $f_1$ is used first for the first 50 time increments with a start value of $x_0=0.5289$. Subsequently there is a transition (see (ii) for details) to mode $f_2$, which becomes steady-state after increment 100 until increment 150. Accordingly, from increment 200 and increment 300 respectively, the mode $f_3$ and $f_4$ is each adopted for 50 increments. This is followed by a transition back to $f_1$. FIG. 1a shows a section (increments 300 to 450) of the time response of the time series $\{x_t\}$ with $x_{t+1}=f(x_t)$.

The segmentation of the first 450 time increments with six predictors $f_i$, i=1, . . . , 6 (RBF networks of the type Moody-Darken) is shown in FIG. 1b. Training produces specialization of four of the predictors (6, 2, 4, 3) each to one of the four modes above. The steady-state regions are at the intervals [0, 50] and [400, 450] ($f_1$), [100, 150] ($f_2$), [200, 250] ($f_3$) and [300, 350] ($f_4$). The other two predictors (3, 5) have specialized to the transition regions between the modes. This shows the drawback of conventional switch segmentation, where, in the case of transitions, the particular time region is multiply subdivided without adequate description.

Instead of the so-called "hard competition" described here, where only one prediction model is optimized in a training step (ie "winner takes all"), it is also possible to alter the degree of competition as part of "soft competition" training, as described in the publication by K. Pawelzik et al.

(ii) Step 2 (Drift Segmentation)

In the second step the transitions (socalled drifting, non-abrupt, sliding change) between the system modes are considered. In the invention, as an important requisite for drift segmentation, it was found that the transition from a first system mode is direct to a second system mode and not by way of a third system mode. Drifting between system modes is thus modeled by superimposition of—or paired linear interpolation between—precisely two modes. In this case mixed, possibly stepped intermediate modes appear, which are not system modes in their own right, ie pure, however.

A set of P pure system modes is considered, each represented by a network k(s), S∈P, and a set of M mixed system modes, each represented by a linear superimposition of two networks i(s) and j(s), s∈M. The model network $g_s$ for a given mode s∈S, S=P∪M is given by $$g_s(\vec{x}_t) = \begin{cases} f_{k(s)}(\vec{x}_t) & \text{for } s \in P \\ a(s)f_{i(s)}(\vec{x}_t) + b(s)f_{j(s)}(\vec{x}_t) & \text{for } s \in M \end{cases} \qquad (2)$$

In (2) $\vec{x}$ is the vector $(x_t, x_{t-\tau}, \ldots, x_{t-(m-1)\tau})$ of the time delay coordinates of the time series $\{x_t\}$ and $f_{i,j}$ are predictors determined according to the above switch segmentation. m is an imbedding dimension and $\tau$ the delay parameter of the imbedding. The imbedding dimension is the dimension of the phase space in which the system is considered and in which the models operate.

Two parameters a, b together with two network indexes i, j are characteristic of each mixed system mode. The number of mixed modes is limited to simplify the calculation effort. A finite number of values a(s) are defined with 0<a(s)<1 and b(s)=1−a(s). For further simplification, equal intervals are selected between the values α(s) according to $$a_r = \frac{r}{R+1} \text{ with } r = 1, \ldots, R \qquad (3)$$

R corresponds to the number of admissible intermediate modes and is also referred to as the resolution or graduation of the interpolation between the pure modes. The resolution R can assume any value, but it is selected sufficiently low as a function of application to achieve optimum system description (especially in heavily noise-corrupted operations) and practicable calculation times, especially in consideration of the switching rate given above. As discussed below in practical applications, it is possible for the resolution R to be selected manually by an operator or automatically by a control circuit as a function of an analysis result and comparison with a threshold value.

The total number of mixed modes is |M|=R·N·(N−1)/2 for a given resolution R between two networks. In the above example the total number of mixed modes is thus |M|=896 for N=8 pure modes and resolution R=32. The eight pure modes are added for determining the total number of system modes.

Drift segmentation now comprises the search for a segmentation with the pure and mixed system modes (a, b, R) that is optimized in terms of the prediction error of the modes of the entire time series. The predictors are chosen so that one of the modes from the total number of system modes can be allocated to each element of the time series. The prediction error is the deviation of a predictor prediction from the actual element of the time series to be investigated. For the time series to be investigated, which is no longer necessarily the training time series with which the matched networks or predictors were determined in switch segmentation, a prediction is determined for each time increment with each of the predictors, resulting in a time-dependent matrix of the predictor predictions from which a mean prediction error can be derived for randomly selected segmentations. The segmentation with the smallest prediction error is the sought drift segmentation.

The search for the segmentation with the smallest prediction error can be made by any suitable search or iteration technique. Preferable is a dynamic programming technique equivalent to the Viterbi algorithm for HM (hidden Markov) models. Details of this are to be found, for example, in the publication "A Tutorial on Hidden Markov Models and Selected Applications in Speech Recognition" of L. R. Rabiner in "Readings in Speech Recognition" (eds. A. Waibel et al., San Mateo, Morgan Kaufmann, 1990, pp 267-296). Where HM models are concerned, drift segmentation is the most probable mode sequence that could have generated the time series to be investigated. As an extra condition, the possibility of mode changes is restricted by the T function, as discussed below.

The aim of the matching is the provision of an optimum sequence of networks or linear mixtures of them. A sequence is optimum when the so-called energy or cost function C* of the prediction is minimized. The cost function C* is composed of the sum of the square-law errors of the prediction and the cost functions of the mode transitions of the sequence. Derivation of the cost function C* between two points in time $t_0$ and $t_{max}$ is inductive, assuming initially a start cost function according to $$C_s(t_0) = \epsilon_s(t_0) \quad (4)$$

where $$\epsilon_s(t) = (x_t - g_s(\vec{x}_{t-1}))^2 \quad (5)$$

is the square-law error of the prediction of the pure or mixed modes g.

For the induction step from t−1 to t, the cost function is computed according to equ. (6) for all s∈S $$C_s(t) = \varepsilon_s + \min_{\hat{s} \in S}\{C_{\hat{s}}(t-1) + T(\hat{s}, s)\}, t = t_0 + 1, \ldots, t_{max} \quad (6)$$

where T ($\hat{s}$, s) is the cost function of the transition from a mode $\hat{s}$ to a mode s.

The optimum (minimum) cost function C* is then $$C^* = \min_{s \in S}\{C_s(t_{max})\} \quad (7)$$

In the HM models the function T corresponds to the transition probabilities and can be selected as suitable for the application. It is possible, for example, to allow abrupt switching transitions and sliding drift between two networks and to eliminate all other transitions by T=∞.

Drift segmentation is produced by the determined optimum sequence of networks or linear mixtures of them in that the modes producing C* are traced back and detected as a function of time.

Drift segmentation can be followed by an extra step of reducing the number of networks used for modeling, this being explained below.

Finally the segmented modes are identified by assigning the related system mode to each predictor or prediction model. This kind of identification is a function of the application.

The result of drift segmentation in the case of the chaotic time series $\{x_t\}$ with four modes that is explained above with reference to FIGS. 1a and b is described in what follows with reference to FIGS. 2a and b. Drift segmentation comprises the search for a response a(t) that produces a special path between the pure modes for which the prediction error of the entire time series is optimized.

The first 50 time increments with the mode according to $f_1$ are followed by 50 increments with a time-linear transition to the mode according to $f_2$. The transition is a time-dependent drift according to $$f(\vec{x}_t) = (1 - a(t))f_1(\vec{x}_t) + a(t)f_2(\vec{x}_t) \quad \text{With} \quad (8)$$

$$a(t) = \frac{t - t_a}{t_b - t_a} \quad t_a = 50, t_b = 100$$

Corresponding transitions occur for 50 increments in each case after the 150th, 250th and 350th increment.

FIGS. 2a and b show the occupancy of the particular modes according to the determined networks as a function of time (time increments [1200, 2400]). For the sake of clarity the transition or drift regions are presented, according to their time limits and outset or end modes, in frames in which the particular drift between the modes is dotted. FIG. 2a shows, for resolution R=32 (see equation 3), transitions as for the time increments 1350 through 1400 between networks 2 and 4. The transitions are linear, as can be expected from equation (8). Lower resolution of R=3 produces the segmentation shown in FIG. 2b. Unlike the linear drift, here the dotted transitions are stepped. Nevertheless, this presentation at lower resolution is still an adequate description of the dynamic response of the system, as a comparison between the timing of the modes and the drift demonstrates.

(2) Application Examples for Detecting Drift Transitions (i) Blood Cell Regulation in the Human Body Blood cell regulation in the human body is a highly dimensional, chaotic system that can be described by the following Mackey-Glass delay differential equation (refer also to the above publication by J. Hertz et al.):

$$\frac{dx(t)}{dt} = -0.1x(t) + \frac{0.2x(t - t_d)}{1 + x(t - t_d)^{10}} \quad (9)$$

Time series of physiological parameters that are characteristic of the set of red blood cells can be segmented as a function of application. The functionality of the segmentation is explained and exemplified below.

Given two modes A and B differing through the respective delay parameters $t_d$=17 and $t_d$=23, there is an initial transition from A to B after 100 increments for a sampling time increment of τ=6. The transition lasts 100 increments and is a superimposition of equation (13) with the two delay parameters $t_d$ during integration of equation (13). The superimposition is produced by an exponential drift parameter a (see equation (2)) according to $$a(t) = \exp\left(\frac{-4t}{100}\right), t = 1, \ldots, 100 \quad (10)$$

Figure 3:
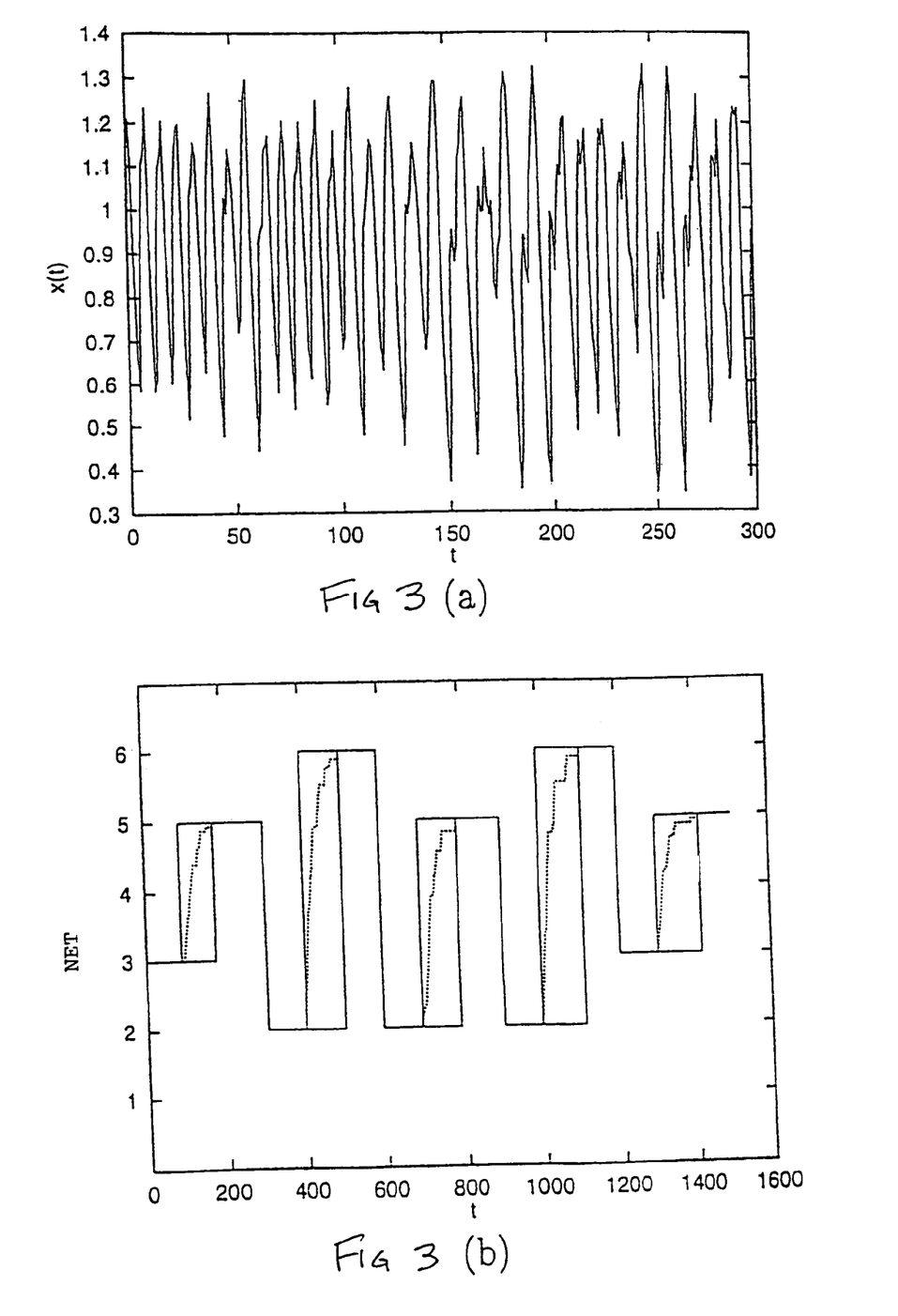
FIGS. 3a-d are graphs including curves of segmentation of blood regulating data after the method, and FIG. 4 Curves of segmentation of EEG data with the method.

As a result, steady-state modes A or B or the particular transitions repeat every 100 increments. A switch-like shift is assumed for each reverse transition after a drift transition. FIG. 3a shows the corresponding time series for 300 increments. Drift segmentation with six predictors on the basis of RBF networks with 40 basis functions each, one imbedding parameter m=6 and the delay parameter τ=1 (see equation (2)) produces the picture in FIG. 3b. The expected segmentation of the time series into steady-state modes and drift transitions is shown.

Nevertheless, two networks have specialized on one mode (2, 3 ⇒mode A, 5, 6 ⇒mode B), respectively. In such a situation the invention provides for the extra step of reducing the number of networks used for modeling.

Figure 3C:
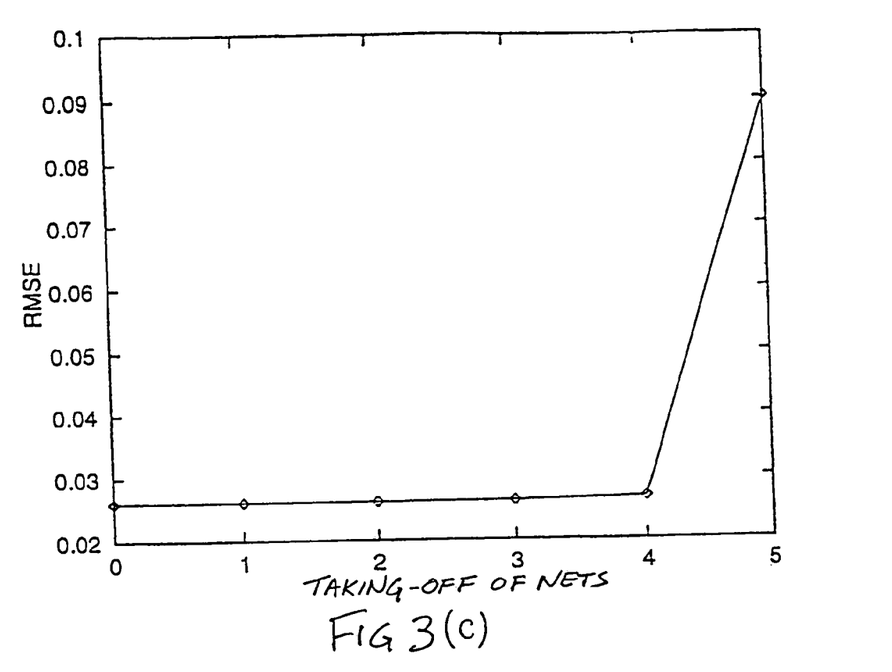

The reduction step comprises sequential reduction of the number of networks, combined in each case with determination of the mean prediction error. Reduction (withdrawal of redundant networks) is ended if continuing reduction of the number of networks means a significant increase in prediction error. FIG. 3c shows the result of such reduction. The root mean square error (RMSE) remains constant when one, two, three and four networks are removed, but there is a sharp rise when modeling with only one network. This means that the system is optimally modeled with a number of networks equal to the total number of networks observed minus the number of redundant networks.

Figure 3D:
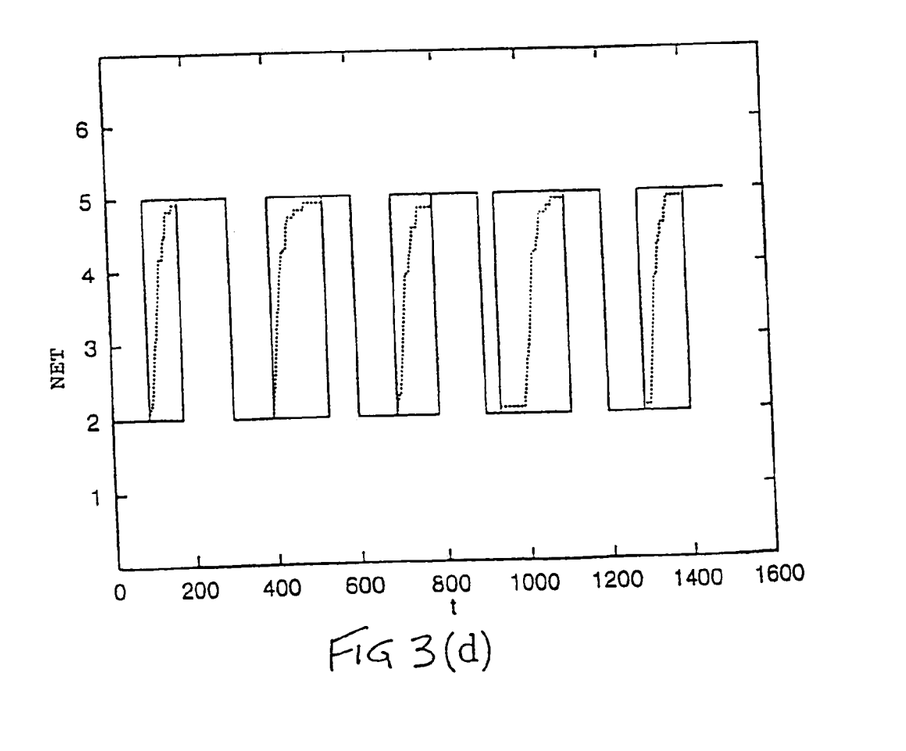

Adequate model networks are obtained by computing the RMSE value for each network combination with a reduced number of networks. The network combination with the smallest RMSE comprises the sought model networks or predictors. FIG. 3d shows drift segmentation after the reduction step. The remaining predictors 2 and 5 describe the system in its entirety.

(ii) Detecting Sleep Data

A further application is to be found in the analysis of physiological data that are characteristic of the sleeping and waking modes of humans. Time series of EEG data, for example, can be segmented as a basis for subsequent procedures to detect sleep disorders.

Figure 4:
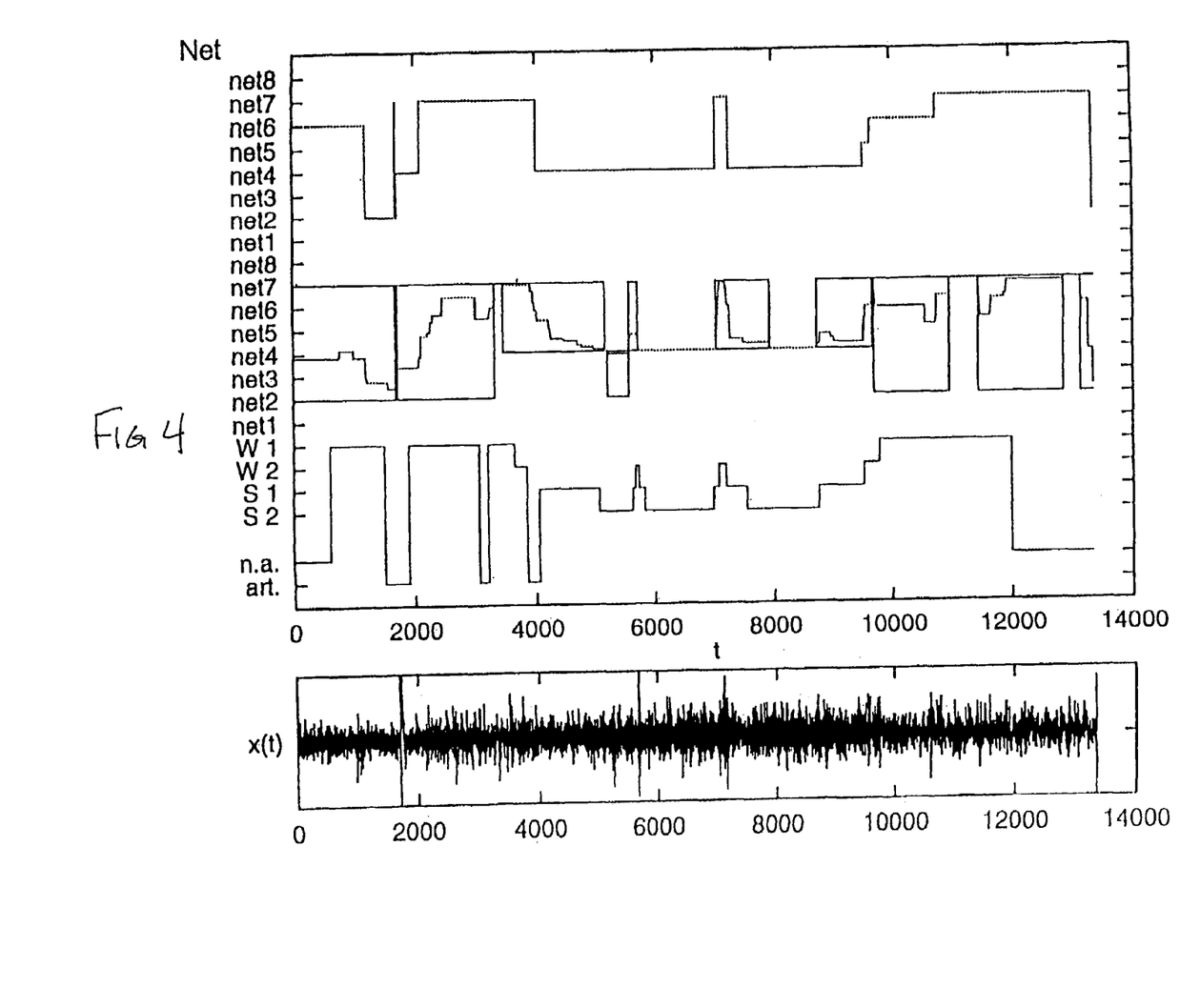

FIG. 4a shows by comparison the results of a conventional switch segmentation (top), a drift segmentation (center) and a "manual" segmentation (bottom) by a medical specialist (sleep researcher) based on empirical values in the example of an afternoon sleep by a healthy person. The switch and drift segmentations are produced with eight networks (net1 through net8) on single-channel EEG data x (t) (FIG. 4b). In FIG. 4a, as in FIG. 2, frames are drawn for the sake of clarity to illustrate between which networks there is interpolation in the drift modes. The dotted line inside the frames indicates the actual response in each case. Manual segmentation is based on the observation of physiological signals (eg EEG, EOG, ECG, pulse, blood pressure, respiration, ocular movement). W1, W2 designate two wake modes with opened and closed eyes, and S1, S2 are sleep states. "n.a." and "art." relate to states or artifacts that are not considered.

Switch segmentation shows a comparatively undifferentiated picture that is only roughly consistent with the other observations. Thus a predomition phase occurs in all three cases at t≈7000. Drift segmentation produces several drift transitions, however, that represent additional details of sleep behavior. The "manually" observed beginning of sleep at t≈4000 is represented by an exponential drift transition from net7 (wake mode predictor) to net4 (sleeping mode predictor). Awaking begins at t≈9000 through a slight drift back to net7, which is maintained until the "manually" determined waking point t≈9500 is reached. In this situation there is a sudden change of the weighting factor, so that net7 takes on greater weighting. After t≈9800 (eyes open) there is a mixture of the two wake mode predictors net7 and net2.

(iii) Further Applications and Advantages

FIG. 4a shows that detailed segmentations can be automatically produced by the method that to date were only possible by observing complex features on the basis of broad experience and intuition. This advantage can be made use of not only in medicine but also in other areas where large amounts of data occur when describing complex dynamic systems. Such areas are physical, chemical and/or biological process engineering, geology, meteorology, climatology, speech detection.

The methods present the following advantages. The observed system can be highly dimensional (ten or more dimensions). The invention allows reduction of the complexity of such a system by observing lower dimensional modes and changing transitions between them. The use of prediction models for segmentation is invariant to changes in the amplitude of detected signals.

Use of the methods for prediction or control of a system works as follows. First, as described above, the actual state of the system is detected from preceding observation and knowledge of the current modes, this possibly being a mixture according to the result of drift segmentation. The actual state corresponds to a dynamic system f. Prediction means that the system f is applied to the momentary state x, resulting in the prediction for the state y that directly follows. Control means that the deviation from a setpoint state is determined from the actual state, and that an appropriate control strategy is derived from the deviation.

The advantage of prediction and control is that in complex systems (for example, detecting chemical reactions in a reactor), possibly only allowing measurement of a few variables, which themselves do not permit direct conclusions about the state of the system and any mixed states that exist because of ambiguities or system-immanent delays, detailed information about the system can nevertheless be derived. Thus, in the example with a chemical reaction, an optimum control strategy, comprising the dosing of certain coreactants, can be derived from detection of the macroscopic, thermodynamic state variables for instance.

The invention claimed is:

1. A method performed on a computer for detecting modes of a dynamic system in a physical, chemical or biological process with a multiplicity of modes $s_i$ that each have a set α(t) of characteristic system parameters comprising the steps of:
   performing a switch segmentation of a time series of at least one system variable x(t), in which the switch segmentation is a simulation of a training time series of the system or of the time series to be investigated with several, competing prediction models, detecting predetermined prediction models $f_i$ for system modes $s_i$ for each system variable x(t) in each time segment of a predetermined minimum length, deriving a system model by performing a drift segmentation subsequent to said switch segmentation in which, in each time segment in which there is a transition of the system from a first system mode $s_i$ to a second system mode $s_j$, a series of mixed prediction models $g_i$ is detected and produced by linear, paired superimposition of prediction models $f_{i,j}$ of the two system modes $s_{i,j}$, detecting a current system mode corresponding to a current state of the dynamic system; and applying the derived system model to the detected current system mode to determine a state of the dynamic system in the physical, chemical or biological process, that directly follows the current state.

2. The method according to claim 1 in which the prediction models are formed by neural networks or other models for estimating functions that are each characteristic of a mode s and compete for description of individual elements of the time series according to predetermined training rules.

3. The method according to claim 1 in which the series of mixed system modes $g_i$ is determined from the prediction models $f_{i,j}$ and interpolation parameters a, b according to $g_i=a(s)f_{i(s)}(x)+b(s)f_{j(s)}(x)$.

4. The method according to claim 1 in which the series of mixed prediction models $g_i$ is detected by determining a prediction for each time increment with each possible prediction models, resulting in a time-dependent prediction matrix from which a mean prediction error for randomly selected segmentations can be derived, whereby a sought series of mixed prediction models $g_i$ is the segmentation with a smallest prediction error or a maximum probability.

5. The method according to claim 1 in which drift segmentation is followed by an additional step to reduce a number of prediction models used for modeling where the number of prediction models is reduced sequentially, associated with a determination of a mean prediction error, until a further reduction of a number of prediction models means an increase in the prediction error.

6. The method according to claim 1 in which the time series of at least one of the system variables x(t) comprises a time series of physiological parameters described by the Mackey-Glass delay differential equation $dx(t)/dt=-0.1x(t)+0.2x(t-t_d)/1+x(t-t_d)^{10}$.

7. The method according to claim 1 in which the time series of at least one of the system variables x(t) comprises a time series of physiological parameters that are characteristic of a development of sleep and wake modes.

8. The method according to claim 1 in which the time series of at least one of the system variables x(t) comprises a time series of speech signals.

9. The method according to claim 3 in which the interpolation parameters are selected according to 0<a(s)<1 and b(s)=1-a(s).

10. The method according to claim 9 in which the values a(s) are restricted to a certain resolution figure R.

11. The method according to claim 9 in which values a(s) are equidistant.

12. The method according to claim 4 in which a search for the segmentation with the smallest prediction error is made by a dynamic programming technique that is equivalent to a Viterbi algorithm for hidden Markov models, whereby an optimum sequence of prediction models is determined using a minimized cost function C* of the prediction and the segmentation is derived inductively from the sequence of prediction models.

13. The method according to claim 7 in which the physiological parameters comprise EEG signals.

14. A method performed on a computer for detecting modes of a dynamic system in a physical, chemical or biological process with a multiplicity of modes s that each have a set α(t) of characteristic system parameters comprising the steps of:

performing a switch segmentation of a time series of at least one system variable x(t), in which the switch segmentation is a simulation of a training time series of the system or of the time series to be investigated with several, competing prediction models, detecting predetermined prediction models $f_i$ for system modes $s_i$ for each system variable x(t) in each time segment of a predetermined minimum length, deriving a system model by performing a drift segmentation subsequent to said switch segmentation in which, in each time segment in which there is a transition of the system from a first system mode $s_i$ to a second system mode $s_j$, a series of mixed prediction models $g_i$ is detected and produced by linear, paired superimposition of prediction models $f_{i,j}$ of the two systems modes $s_{i,j}$, and controlling said dynamic system in the physical, chemical or biological process, via determining a deviation of a current state of said dynamic system from a setpoint state using the derived system model and deriving a control strategy on the basis of said deviation.

15. The method according to claim 14 in which the prediction models are formed by neural networks or other models for estimating functions that are each characteristic of a mode s and compete for description of individual elements of the time series according to predetermined training rules.

16. The method according to claim 14 in which the series of mixed system modes $g_i$ is determined from the prediction models $f_{i,j}$ and interpolation parameters a, b according to $g_i=a(s)f_{i(s)}(x)+b(s)f_{j(s)}(x)$.

17. The method according to claim 14 in which the series of mixed prediction models $g_i$ is detected by determining a prediction for each time increment with each possible prediction models, resulting in a time-dependent prediction matrix from which a mean prediction error for randomly selected segmentations can be derived, whereby a sought series of mixed prediction models $g_i$ is segmentation with a smallest prediction error or a maximum probability.

18. The method according to claim 14 in which drift segmentation is followed by an additional step to reduce a number of prediction models used for modeling where the number of prediction models is reduced sequentially, associated with a determination of a mean prediction error, until a further reduction of the number of prediction models means an increase in the prediction error.

19. The method according to claim 14 in which the time series of at least one of the system variables x(t) comprises a time series of physiological parameters described by a Mackey-Glass delay differential equation $dx(t)/dt=-0.1x(t)+0.2x(t-t_d)/1+x(t-t_d)^{10}$.

20. The method according to claim 14 in which the time series of at least one of the system variables x(t) comprises a time series of physiological parameters that are characteristic of a development of sleep and wake modes.

21. The method according to claim 14 in which the time series of at least one of the system variables x(t) comprises a time series of speech signals.

22. The method according to claim 16 in which the interpolation parameters are selected according to $0<a(s)<1$ and $b(s)=1-a(s)$.

23. The method according to claim 17 in which a search for the segmentation with the smallest prediction error is made by a dynamic programming technique that is equivalent to a Viterbi algorithm for hidden Markov models, whereby an optimum sequence of prediction models is determined using a minimized cost function C* of the prediction and the segmentation is derived inductively from a sequence of prediction models.

24. The method according to claim 20 in which the physiological parameters comprise EEG signals.

25. The method according to claim 22 in which the values a(s) are restricted to a certain resolution figure R.

26. The method according to claim 22 in which values a(s) are equidistant.

* * * * *